US010359369B2

(12) United States Patent
Barak et al.

(10) Patent No.: US 10,359,369 B2
(45) Date of Patent: Jul. 23, 2019

(54) METROLOGY TEST STRUCTURE DESIGN AND MEASUREMENT SCHEME FOR MEASURING IN PATTERNED STRUCTURES

(71) Applicant: NOVA MEASURING INSTRUMENTS LTD., Rehovot (IL)

(72) Inventors: Gilad Barak, Rehovot (IL); Oded Cohen, Gedera (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 185 days.

(21) Appl. No.: 15/502,329

(22) PCT Filed: Aug. 6, 2015

(86) PCT No.: PCT/IL2015/050807
§ 371 (c)(1),
(2) Date: Feb. 7, 2017

(87) PCT Pub. No.: WO2016/020925
PCT Pub. Date: Feb. 11, 2016

(65) Prior Publication Data
US 2017/0227474 A1    Aug. 10, 2017

Related U.S. Application Data

(60) Provisional application No. 62/034,239, filed on Aug. 7, 2014.

(51) Int. Cl.
*G01N 21/956* (2006.01)
*G01B 11/14* (2006.01)
(Continued)

(52) U.S. Cl.
CPC ............ *G01N 21/956* (2013.01); *G01B 11/14* (2013.01); *G01R 31/309* (2013.01); *H01L 22/30* (2013.01);
(Continued)

(58) Field of Classification Search
CPC .. G01N 21/956; G01B 11/14; G01B 2210/56; H01L 23/544; H01L 22/30
See application file for complete search history.

(56) References Cited

U.S. PATENT DOCUMENTS

| 5,422,723 A | 6/1995 | Paranjpe et al. |
| 2008/0311344 A1 | 12/2008 | Marie Kiers et al. |
| 2011/0014786 A1* | 1/2011 | Sezginer ............ G06F 17/5077 438/618 |

FOREIGN PATENT DOCUMENTS

WO    05069082    7/2005

* cited by examiner

*Primary Examiner* — Hina F Ayub
*Assistant Examiner* — Amanda Merlino
(74) *Attorney, Agent, or Firm* — Browdy and Neinmark, PLLC

(57) ABSTRACT

A test structure is presented for use in metrology measurements of a sample pattern. The test structure comprises a main pattern, and one or more auxiliary patterns. The main pattern is formed by a plurality of main features extending along a first longitudinal axis and being spaced from one another along a second lateral axis. The one or more auxiliary patterns are formed by a plurality of auxiliary features associated with at least some of the main features such that a dimension of the auxiliary feature is in a predetermined relation with a dimension of the respective main feature. This provides that a change in a dimension of the auxiliary feature from a nominal value affects a change in non-zero order diffraction response from the test structure in a predetermined optical measurement scheme, and this change is indicative of a deviation in one or more parameters of the main pattern from nominal value thereof.

24 Claims, 8 Drawing Sheets

(51) Int. Cl.
  *G01R 31/309* (2006.01)
  *H01L 23/544* (2006.01)
  *H01L 21/66* (2006.01)
(52) U.S. Cl.
  CPC ........ *H01L 23/544* (2013.01); *G01B 2210/56* (2013.01)

METROLOGY TEST STRUCTURE DESIGN AND MEASUREMENT SCHEME FOR MEASURING IN PATTERNED STRUCTURES

TECHNOLOGICAL FIELD

The present invention is generally in the field of optical metrology, and relates to a design of a test structure and measurement method and system utilizing such test structure for metrology measurements in patterned structures, such as semiconductor wafers having a grating.

BACKGROUND

Microelectronic devices are widely used and are becoming smaller in dimensions as well as more complex. Manufacturing of such microelectronic devices requires accurate inspection and metrology to identify appropriate patterns on substrates (e.g. wafer substrates), as well as identify defects in such patterns. Generally, the structure's properties (geometry and material composition) can be determined by analyzing the optical response of the structure at different wavelengths, different polarization states and/or different directions.

Accurate characterization of the geometrical and material properties of microelectronic devices becomes increasingly challenging, as the critical dimensions become ever smaller and the devices become more complex. Optical reflectometry (including spectral reflectometry and spectral ellipsometry) is an extremely effective method for obtaining information on the geometry and material properties of such structures. In this method, broadband light is shone on a sample and collected after being reflected from it. By analyzing the specular reflectance of different wavelengths and polarization components of the incident light, incident at different directions, it is possible to obtain information about the structure/sample. Commonly, optical reflectometry is applied to test structures comprised of a repeating array of identical elements, e.g. grating.

Metrology is commonly used to identify specific attributes of the measured structure, such as geometric parameters or material characteristics, and typically utilize spectral measurements. The accuracy by which these parameters can be measured is directly determined by their effect on the measured spectra.

GENERAL DESCRIPTION

There is a need in the art to increase the sensitivity to parameters of interest, possibly on account of the sensitivity to those parameters which are of a less interest (e.g. not required for the monitoring process).

The present invention provides a novel approach which can be used for process control, e.g. patterning process. For example, the technique of the invention can be used for identifying misalignment of patterned layers in a corresponding production structure, like in case of overlay, double- or multi-patterning, SADP, SATP etc. More specifically, the invention is highly suitable to modern applications involving split division processes.

As indicated above, metrology methods are used for determining parameters of a sample (geometric parameters and materials characteristics of the pattern in the sample), while the accuracy of measuring these parameters is directly determined by the effect of these parameters on measured optical response (e.g. spectral response). It is hence of great interest to be able to increase the sensitivity of measurements to parameters of interest, possibly at the price of the sensitivity to those parameters which are not of interest or of less interest for the monitoring process. Those parameters for which small changes in value have a strong effect on the measured reflection from the sample (optical response) are commonly termed 'strong', and can be monitored with great accuracy. Conversely, 'weak' parameters are those which have a small effect on the measured reflection (optical response), and their accurate metrology is highly challenging. It should be noted that the terms "reflected" and "reflection" as used in the present application should interpreted broadly as "optical response to illumination", and include specular and non-specular reflection such as scattering.

The present invention provides a novel approach by which sensitivity of optical measurements to a change in parameters of interest is significantly increased. To this end, the invention provides several design principles for the configuration of a metrology test structure. It should be noted that a test structure is associated with a real structure/sample to be measured/inspected, i.e. the manufacture of the test structure has common steps with that of the real sample. Considering semiconductor industry, the test structure is typically located within a margins or scribe lines of the wafer (real sample).

According to the invention, the test structure is configured for optical measurements using a dark-field (DF) measurement mode. This provides for highly sensitive, ultra-low background noise measurement of the parameters of interest.

The test structure is designed so as to include a main pattern corresponding to the sample pattern, and at least one large-pitch or large-periodicity auxiliary pattern with periodicity (pitch/period) significantly larger than that of the main pattern, so that a high order diffraction from the test structure can be directed onto the light collection path.

Thus, according to one broad aspect of the invention, there is provided a test structure for use in metrology measurements of a sample pattern. The test structure comprises: a main pattern formed by a plurality of main features extending along a first longitudinal axis and being spaced from one another along a second lateral axis; and a plurality of auxiliary features defining at least one auxiliary pattern. The auxiliary features are associated with at least some of the main features such that a dimension of the auxiliary feature is in a predetermined relation with a dimension of the respective main feature, thereby providing that a change in the dimension of the auxiliary feature from a nominal value affects a change in non-zero order diffraction response from the test structure, in a predetermined optical measurement scheme, and this change is indicative of a deviation in one or more parameters of the main pattern from nominal value thereof.

In some embodiments, the auxiliary features of the auxiliary pattern are arranged in a spaced-apart relationship along the second lateral axis, with a pitch/period of the auxiliary pattern being significantly larger than a pitch/period of the main pattern. The auxiliary feature of the auxiliary pattern may be a groove of a substantially V-shaped cross section between two locally adjacent features of the main pattern, a lateral dimension of the groove reducing along a depth of the groove from a top surface of the main pattern according to a predetermined function. The test structure may be configure such that the main features of the main pattern comprise grooves spaced by projections, and auxiliary features are associated with some of the grooves, modifying them to form the V-shaped cross section.

In some embodiments, the auxiliary features of the auxiliary pattern are arranged in the spaced-apart relationship along the first longitudinal axis.

In some embodiments, the auxiliary features of the auxiliary pattern are located in the features of the main pattern and are configured such that the lateral dimension of the auxiliary feature matches the lateral dimension of the respective feature of the main pattern.

In some embodiments, the main pattern comprises at least first and second sub-patterns formed by at least first and second arrays of the main features arranged in an alternating manner along the second lateral axis. The plurality of the auxiliary features may define at least first and second auxiliary patterns associated with, respectively, the at least first and second sub-patterns, and the auxiliary features of each auxiliary pattern are arranged in a spaced-apart relationship along the first axis with periodicity significantly larger than a periodicity of the main features of the same sub-pattern along the second axis. Moreover, the first and second auxiliary patterns are shifted with respect to each other by a predetermined distance along the first axis.

The auxiliary patterns may be of the same periodicity. The shift by the predetermined distance between the auxiliary patterns may be approximately equal to half of the periodicity of the auxiliary pattern.

A change in the lateral dimension of the auxiliary feature of one auxiliary pattern with respect to that of the other auxiliary pattern affects the non-zero order diffraction response from the test structure, being thus indicative of a change in the lateral dimension of the main feature from the nominal value.

The first and second shifted auxiliary patterns define a combined pattern having a unit cell. A change in the lateral dimension of the auxiliary feature of one auxiliary pattern with respect to that of the other auxiliary pattern modifies the unit cell of the combined pattern, thereby affecting the non-zero order diffraction response from the test structure, being indicative of a change in the lateral dimension of the main feature from the nominal value.

Additionally, in some embodiments, the lateral dimensions of the main features of the first and second sub-patterns may be different from one another by a predetermined known value.

The measured non-zero order of diffraction may include at least one of first and second orders of diffraction.

The test structure may be located in a test site (e.g. in a scribe line) in a semiconductor wafer.

Thus, the invention also provides a sample (e.g. a semiconductor wafer) comprising a sample pattern and at least one test site, each comprising the above-described test structure.

According to a further aspect of the invention, there is provided a method for use in measurements of a sample pattern. The above described test structure is provided in association with the sample pattern to be measured. An optical measurement is performed on the test structure, at least one non-zero order diffractive response from the test structure is detected, and measured data indicative thereof is generated. The measured data is processed and analyzed, and upon identifying a change in the diffractive response, data indicative of deviation of one or more parameters of the sample pattern from nominal value is generated.

The method may be used for controlling a patterning process applied to the sample to create the sample pattern. This may be a multiple patterning process in which two or more arrays of feature are created in different patterning stages forming together the sample pattern.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The invention provides a specifically designed novel test structure for use in monitoring/controlling parameters of a sample pattern with which said test structure is associates, e.g. is located in a test site on the sample. The test structure is configured such as to create a link between non-zero order(s), e.g. high orders, of diffraction in a diffractive response of the test structure and one or more parameters of interest in the sample pattern. To this end, the test structure has a main pattern, and auxiliary pattern(s). The main pattern corresponds to the sample pattern (real structure). In the simplest case, the main pattern of the test structure is created/manufactured concurrently with the creation of the sample pattern such that behavior of the test structure parameter(s) during the manufacturing reflects the behavior of parameter of interest in the sample pattern. The auxiliary pattern(s) is/are intentionally formed being configured such that high order diffraction occurs from the test structure (main and auxiliary patterns) and can be detected to provide information about the parameter(s) of the main pattern, and accordingly about the parameter(s) of the sample pattern. As will be exemplified further below, the main pattern of the test structure may be identical to that of the sample pattern; or may be in a known relation with the sample pattern (i.e. the feature of the main pattern may different from the respective feature of the sample pattern by a known value/function).

Figure 1:
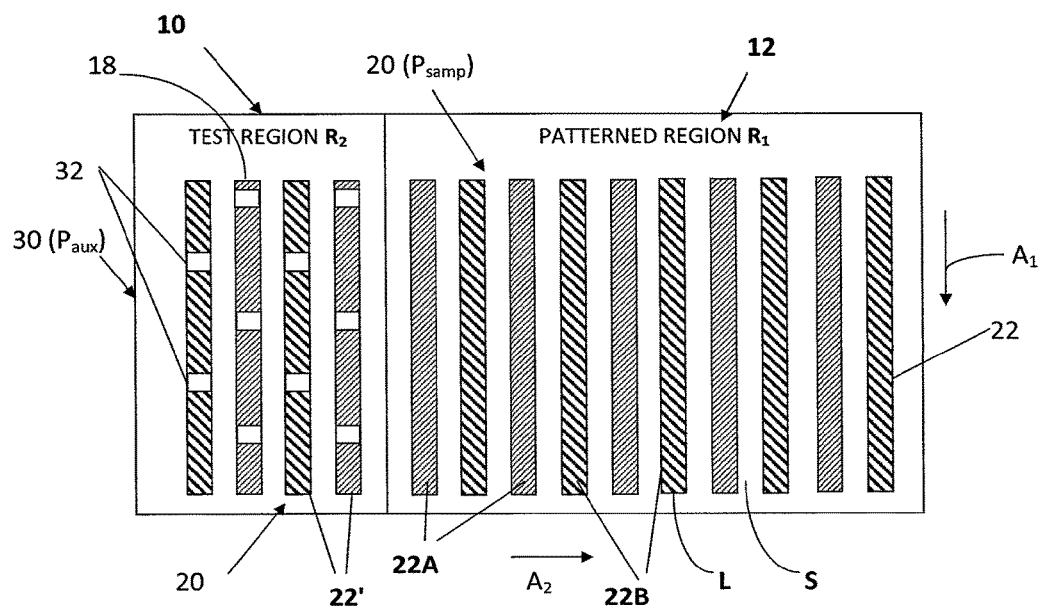
FIG. 1 schematically illustrates the principles of the invention for the configuration of the test structure.

Reference is made to FIG. 1 schematically illustrating the principles of the invention. A test structure 10 is schematically illustrated, which is associated with a patterned sample 12. In this example, the test structure 10 is integral with the sample, and is located in a test region thereof (usually on scribe lines). More specifically, the sample has a patterned region $R_1$ (constituting a real patterned structure) in which a real pattern or sample pattern $P_{samp}$ 20 is formed, and a test region $R_2$ in which a test structure 10 is located.

It should be understood that the figure is very schematic (e.g. the test site and sample pattern region may not be adjacent), and is not in scale, in order to facilitate illustration and explanation. The figures actually show a small fraction of the pattern sample, as well as a small fraction of the test region.

The sample pattern 20 in the real patterned structure region $R_1$ is a grating typically including a plurality of features arranged with a periodicity of unit cells. The features may be lines L spaced by spaces S. The features (lines and spaces) extend along a first longitudinal axis $A_1$ and are arranged (spaced from one another) along the second lateral axis $A_2$ (pattern axis). The test structure could be configured for controlling one or more parameters of the sample pattern, e.g. the width of line L and/or the width of space S.

As indicated above, the present invention can be used for monitoring the multi-stage patterning process, such as the Spacer Assisted Double Patterning (SADP) technique. Such techniques utilize the principles of pitch division typically aimed at producing the final pattern with very small and dense features. The entire pattern (sample pattern) is formed by two or more arrays (sub-patterns) of features created using sequential patterning stages. This result in such undesirable effect as "pitch walking", which should be controlled. Thus, in the present not limiting example, the sample pattern includes first and second arrays 22A and 22B located in an alternating fashion.

The test structure 10 has a test pattern 18 formed by a main pattern $P_{main}$ which corresponds to (behavior in a predetermined relation with and/or similar to) the sample pattern 20, and is formed by a plurality of main features 22' extending along the first longitudinal axis $A_1$ and being spaced from one another along a second lateral axis $A_2$, and a plurality of auxiliary features 32. The auxiliary features 32 are arranged to define one or more auxiliary patterns, $P_{aux}$, generally designated 30. The auxiliary features 32 are located in at least some of the main features 22 such that a lateral dimension (width) of the auxiliary feature 32 is in a predetermined relation with a lateral dimension of the respective main feature 22'.

Thus, in this specific example of the sample pattern produced by a pitch division multi-patterning process, the main pattern $P_{main}$ in the test structure 10 includes first and second sub-patterns (e.g. produced during different manufacturing steps). These first and second sub-patterns define the first and second alternating arrays 22A and 22B of the main features.

It should, however, be understood that the invention is neither limited to the control of multi-stage patterning process nor to any specific arrangement of features of the sample pattern, provided that the main pattern in the test structure corresponds to the sample pattern to be controlled.

It should be understood that the test structure 10 (e.g. located in the test region $R_2$ of the sample) undergoes the same patterning process as the sample (patterned region $R_1$ of the sample). Accordingly, the arrangement of features of the main pattern $P_{main}$ in the test structure is the same as in the patterned region $R_1$ of the sample, while the auxiliary pattern $P_{auxil}$ is being intentionally created in the test structure (only in the test region $R_2$).

The arrangement of the auxiliary features with respect to the main pattern is such that, when applying optical measurements to the test structure using a predetermined optical measurement scheme, a non-zero order diffraction response of the test structure is indicative of the parameter(s) of interest of the sample pattern. More specifically, a change in the lateral dimension of the auxiliary feature from a nominal value affects a change in the non-zero order diffraction response of the test structure from certain nominal/reference diffraction signature. This change is mainly associated and is thus indicative (mainly) of a change in one or more parameters of interest of the main pattern from nominal value(s) thereof. Examples of the test structures configured according to the invention will be described more specifically further below.

Generally, the invention provides a test structure enabling to use dark field signals for highly sensitive, ultra-low background noise measurement of the parameters of interest. Modern semiconductor devices are based on periodic structures, with pitch determined by the technology node. In today's advanced technology nodes, the pitches used are very small, e.g. dozens nm or even less (7 nm node already under test). Consequently, for standard broadband metrology (UV-Vis-IR), only the zero (specular) diffraction order is reflected, or very few high-order (non-specular) diffraction orders at most.

The present invention provides a test structure, which includes a main pattern that corresponds to the sample pattern, e.g. is similar to the sample pattern (generally behaves similar to the sample pattern), and is further modified by the intentionally produced at least one auxiliary pattern. The auxiliary pattern(s) is/are configured and arranged with respect to the main pattern in such a way that gives rise to a non-zero order diffraction dark-field signal from the test structure, which is highly sensitive to the parameter of interest. In this respect, the non-specular dark field signal is created through reflection of high diffraction orders. This is achieved by superimposing an auxiliary patter, which is a relatively large-pitch pattern, onto the main pattern, which supports reflected high orders. Then, dark field metrology can be used, where only non-specular reflections are collected.

Figure 2:
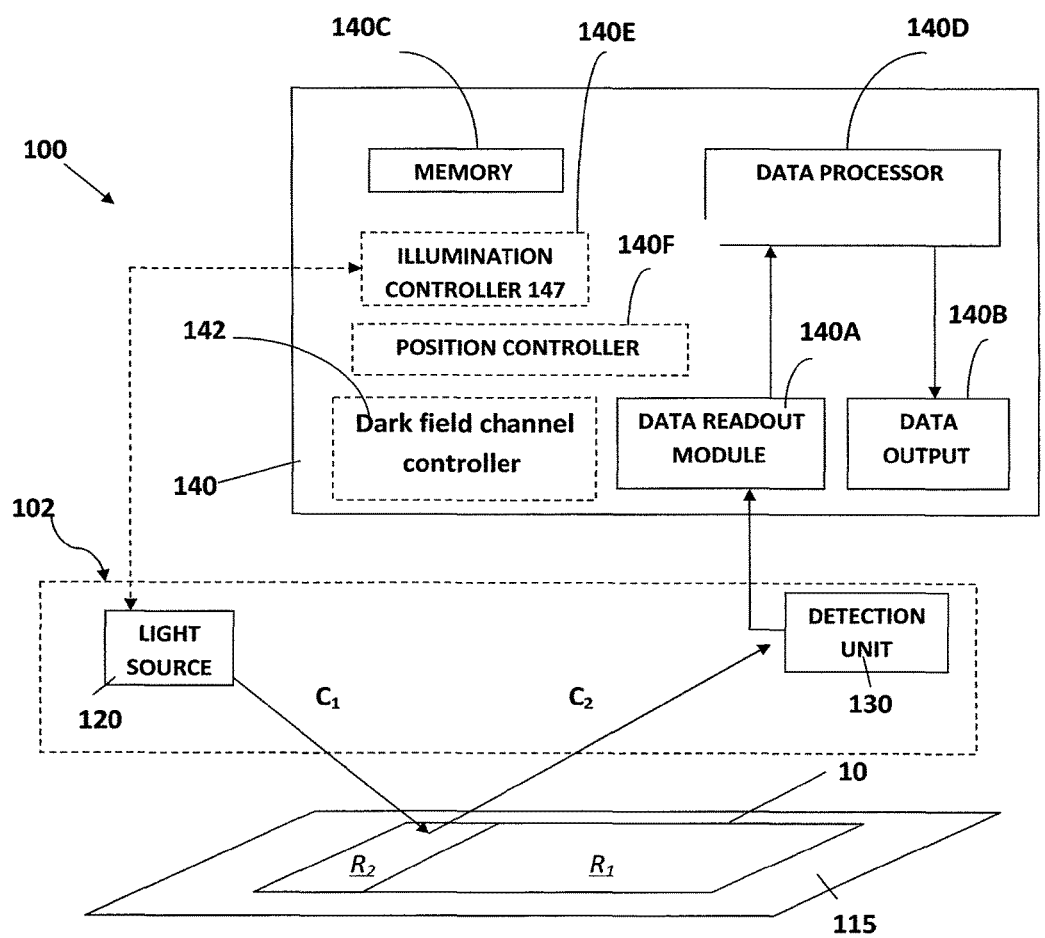
FIG. 2 schematically illustrates the measurement system suitable for implementing dark field measurements on the test structure of the invention.

Reference is made to FIG. 2 illustrating schematically, by way of a block diagram, a measurement system 100 of the invention configured and operable for measuring on the test structure 10. In this non-limiting example, the test structure 10 is located in a test region $R_2$ of a sample.

The measurement system 100 includes an optical unit 102 accommodated with respect to a sample holder 115, and connectable (via wires or wireless signal transmission) with a control unit 140.

The optical unit 102 includes illumination and detection assemblies which define an illumination channel $C_1$ and a collection/detection channel $C_2$. The illumination channel includes a light source unit 120 configured and operable to illuminate, through the illumination channel $C_1$, the test region $R_2$ in which the test structure 10 is located. The detection assembly includes a detection unit 130 configured and operable to receive light returned from the test structure and propagating along the collection/detection channel $C_2$.

The optical unit 102 is configured to implement dark-field mode, namely to detect substantially non-zero order diffraction pattern from the test structure. To this end, any suitable light propagation scheme can be used, including masked light-path scheme can be used, as will be exemplified further below.

The control unit 140 is typically an electronic device including inter alia such software/hardware utilities/modules as data input (or data readout) module 140A and data output 140B, memory 140C, and data processor 140D. The control unit 140 may also include a dark field controller 142 (configured and operable in accordance with the dark-field scheme being used), as well as an illumination controller 140E and/or a position controller 140F.

The control unit 140 is configured to receive and process measured data provided by the detection unit 130 as will be described further below, and may be configured to operate the optical unit, e.g. its dark field scheme (e.g. the detection channel) and/or the light source unit 120. The position controller 140F may be configured for controlling a relative accommodation between the sample holder 115 and at least some elements of the optical unit 102, e.g. for providing measurements on preset or desired locations on the sample, as well as providing a desired orientation of an inspection plane, and/or relative orientation of the illumination and detection channels.

The data processor utility 140D (software utility) of the control unit 140 is adapted (preprogrammed) to analyze the detected light indicative of the high order diffraction data and identify whether it deviates from certain nominal/reference diffraction pattern. As will be described further below, the deviation is caused by a change in one or more parameters of the main pattern (sample pattern).

Figure 3A:
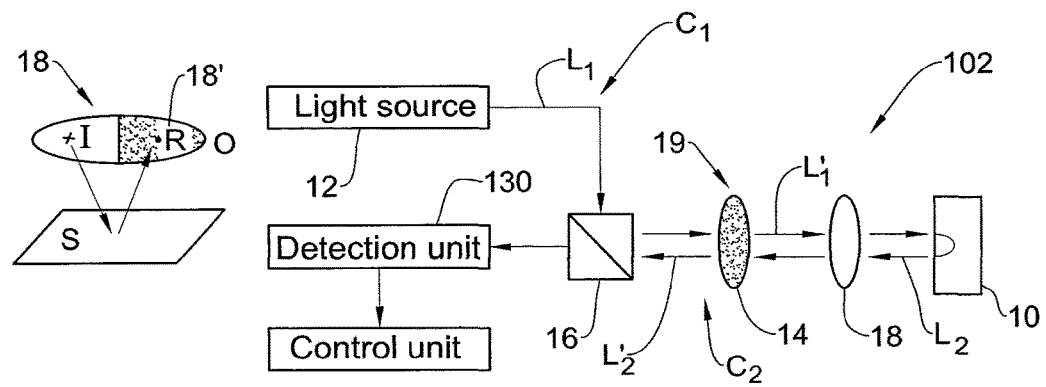
FIGS. 3A and 3B show two examples of an optical unit suitable to be used in the system of FIG. 2 for implementing the dark field measurement scheme based on masked light-path approach.
Figure 3B:
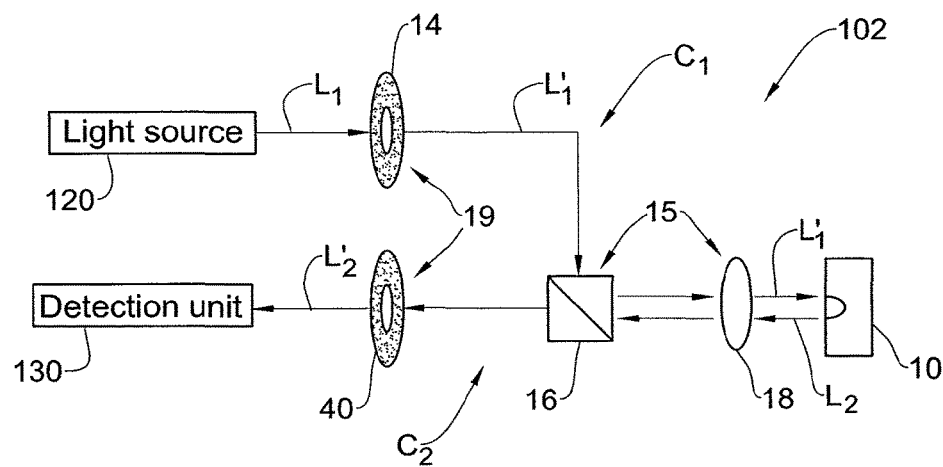

Reference is made to FIGS. 3A and 3B exemplifying various possible configurations of the light propagation scheme in the optical unit 102 using masked light-path scheme. To facilitate illustration and understanding, the same reference numbers are used for identifying components that are common in all the examples.

In the example of FIG. 3A, a dark field (non-zero order) detection mode is achieved by affecting propagation of light through the illumination and detection channels, using a common pattern in the illumination and detection channels. The optical unit 102 includes a light source unit 120, a detection unit 130, and a suitable light directing arrangement including a beam splitter 16 and focusing optics (objective) 18. Light $L_1$ from the light source 120 is directed onto the sample along the illumination path $C_1$ and is reflected by the beam splitter 16 onto a partially blocking mask 14. Light $L'_1$ emerging from the mask 14 is focused by objective 18 onto the sample. Light $L_2$ returned from the illuminated sample is collected by objective 18 and focused onto the mask 14, and light $L'_2$ transmitted by the mask is then transmitted by the beam splitter 16 to the detection unit 130. As shown in the figure, if half 18' of the objective lens aperture 18 is rendered opaque, incident light ray I is specularly reflected from a flat surface S into a point R in the opaque half of the aperture, and is thus blocked. Only rays having their propagation direction altered by the sample (i.e. propagates with angles outside the propagation direction of the specular reflection due to diffraction) can be collected, implementing a dark field (non-zero orders) measurement. In other words, a mask located in the common illumination and detection path can be appropriately designed to block the zero-order diffraction and thus implement the dark-field detection mode.

In the example of FIG. 3B the optical unit 102 is configured such that a dark field (non-zero order(s)) detection mode is achieved by affecting propagation of light through the illumination and detection channels, by placing complementary masks in the illumination and collection channels. Light $L_1$ from the light source 120 passes through the illumination mask 14, and light portion $L'_1$ transmitted through the central region of the mask 14 is directed onto the sample by the beam splitter 16 and objective 18. Reflected light $L_2$ is collected by the objective 18 and transmitted by beam splitter 16 onto the collection mask 40. Light portion $L'_2$ that passes through the transparent periphery region of the mask 40 is detected by the detector 130. In this implementation, the incident light path is partially blocked by the mask 14, leaving a circular transparent region in the center of the field. A conjugate mask 40, blocking the central circular region is used in the detection light path $C_2$, so that light specularly reflected from the sample flat horizontal surfaces is blocked and only light that was diffracted by the test structure is collected. Again, in order to avoid bright-field contribution, the masks are designed to have an overlap. Contrary to the methods based on a single mask described above, in this approach the cylindrical symmetry is maintained.

Figures 3C, 3D:
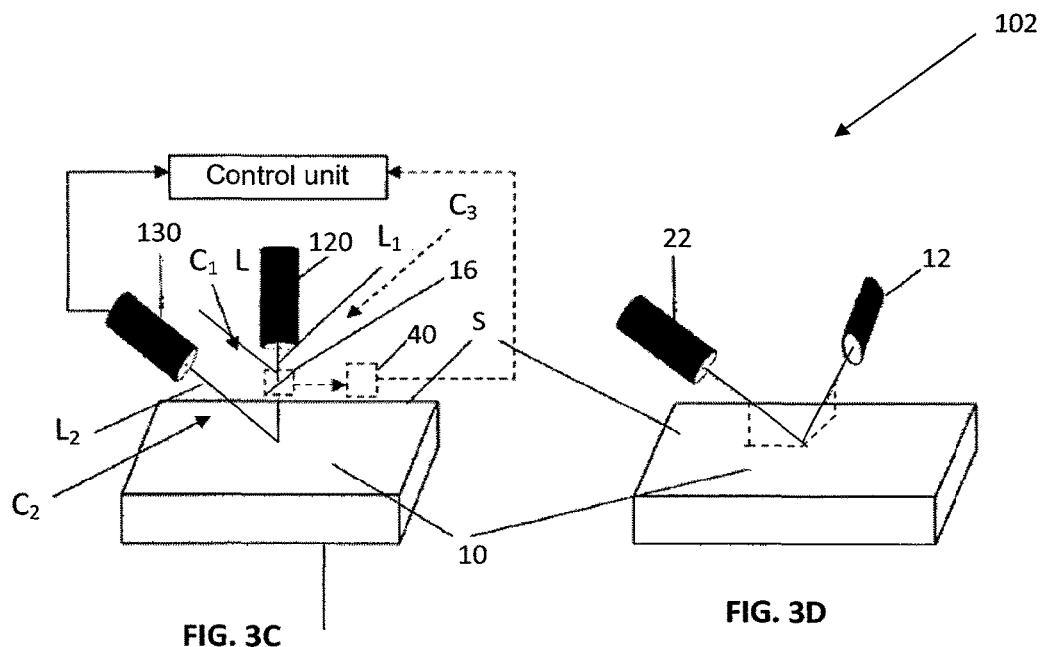
FIGS. 3C to 3E show three examples of an optical unit suitable to be used in the system of FIG. 2 for implementing the dark field measurement scheme based on separation between the illumination and collection channels.
Figure 3E:
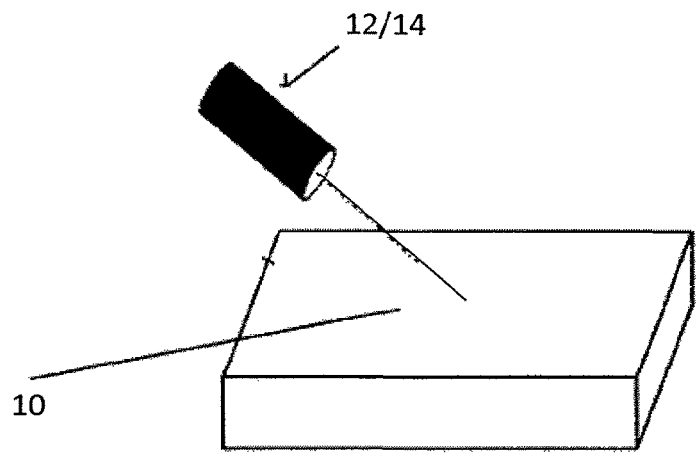

FIGS. 3C to 3E, schematically illustrate examples of the configuration and light propagation scheme in the optical unit utilizing dark field (non-zero order(s)) measurement based on separate illumination and collection paths. In this approach, a dark field measurement is implemented by illuminating the sample in one direction, and placing a detector at an orientation that does not collect light specular reflection from the surface.

According to one possible example, one oblique and one normal channels can be used. The illumination is incident on the test structure in the normal direction and a separate detector is placed at an oblique angle, or vice versa. As shown in FIG. 3C, light $L_1$ coming from a light source 120 is incident perpendicular to the sample surface and light $L_2$ to be detected by detection unit 130 is collected in an oblique angle. This configuration can be reversed, so that light is incident in an oblique angle and collected in perpendicular to the surface. This way, only light diffracted by the test pattern into non-zero order(s) can be collected by the detector.

According to another example shown in FIG. 3D, two oblique channels are used. Light is incident and collected at the same angle a with respect to the surface, but at different azimuths, so that light specularly reflected from the surface is not collected. It should be noted that also two oblique channels with different oblique angles could be used to provide collection of non-zero order(s) diffraction signals, e.g. ±1, etc.).

According to yet another example of FIG. 3E, a single oblique illumination and collection path can be used. Light is incident on the test structure at an oblique angle, and collected at the same direction.

Generally, all implementations are based on illuminating light onto the sample at some angle of incidence. A collection path $C_2$ is set so that it does not collect the specular reflection (zero order). The test structure includes a large-pitch auxiliary pattern, such that high diffraction order(s) (non-zero order(s)) is directed onto the collection path.

For simplicity, in the description below, situations when the large-pitch grating period is set in the direction perpendicular to the plane of incidence, i.e. the measurement plane is oriented substantially perpendicular to the pattern axis or second lateral axis ($A_2$ in FIG. 1). It should, however, be understood that this assumption is not crucial for the applicability of the technique of the invention, and other possibilities are equally applicable. If this assumption is not satisfied, the reflected high diffraction orders are oriented in a direction outside the incidence plane, and the collection aperture in the detection channel $C_2$ is to be adequately placed so as to collect them.

As indicated above, the invention provides a test structure which includes the main pattern (sample pattern) and the relatively large-pitch auxiliary pattern(s) giving rise to a non-zero order(s) (dark field) signal from the test structure.

Let us consider an optical system where the sample is illuminated at a range of angles $\theta_{in}$ and the collection channel collects reflected radiation in the angular range $\theta_{out}$. The large pitch auxiliary structure (one or more auxiliary patterns) added to the main pattern has pitch $\Lambda$. The reflected diffraction orders are distributed along angles $$\theta = \sin^{-1}(\sin(\theta_{in}) + m \cdot \lambda/\Lambda),$$

where $\lambda$ is the wavelength and m is an integer enumerating the diffraction order. Put differently, the $m^{th}$ diffraction order will be scattered from the illumination into the collection channel, for the wavelength range satisfying the following equation:

$$\lambda \in (\sin \theta_{out} - \sin \theta_{in}) \cdot \Lambda/m. \quad (1)$$

It should be noted that when the angular distributions $\theta_{in}, \theta_{out}$ represent a range of allowed angles, there is a range of wavelengths for which the high reflected diffraction order(s) is collected. In order to optimize the test structure design, the implemented large pitch $\Lambda$ is selected so as to guarantee that the high-order(s) reflection is collected by the optical system at a wavelength range where the reflected signal is strong.

It is furthermore possible that the nominal test structure (before the modification according to the invention) will reflect high diffraction orders into the collection channel, for some wavelength range $\lambda_S^{min} < \lambda < \lambda_S^{max}$ or several such ranges. In this case, the value of $\Lambda$ can be chosen so that the wavelength span described in Eq. 1 does not overlap this range.

In order to clarify how to achieve such target design in practice, several specific examples of the test structure are described below with reference to FIGS. 4 and 5A-5C.

Generally, the auxiliary structure introduces a pattern of a new periodicity ($\Lambda$) which for example lies in the same dimension (FIG. 4) as the original period (P) of the main pattern (corresponding to the sample pattern), e.g. printed grating. The "large-period structure" is set so that it is highly sensitive to the parameter of interest (and preferably weakly sensitive to other parameters). Then, the collected dark field signal can be used to obtain an accurate probe to the parameter of interest, which is significantly less correlated to other parameters characterizing the sample.

Figure 4:
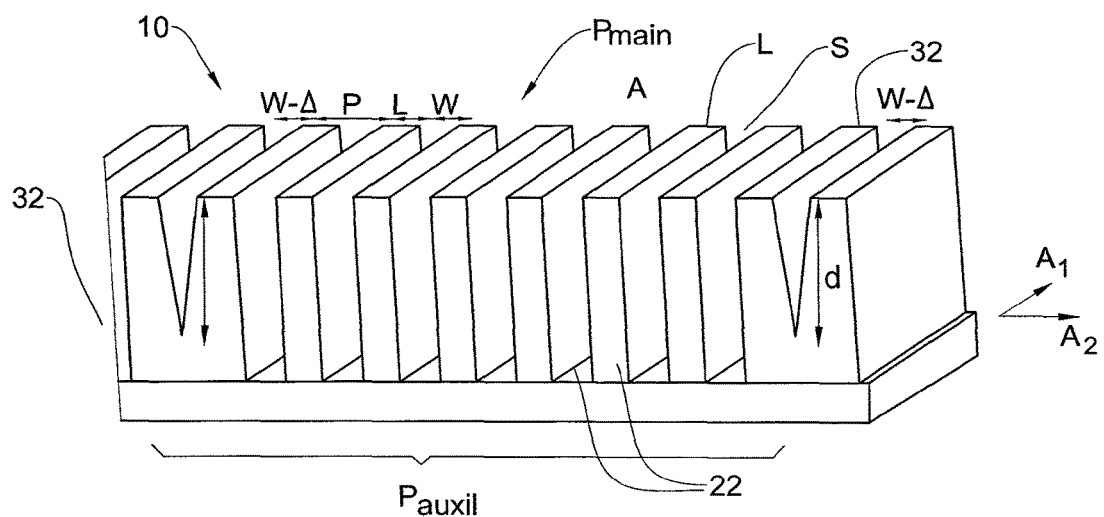
FIG. 4 exemplifies a test structure according to some embodiments of the invention.

FIG. 4 presents an example for such a test structure design. In this specific but not limiting example, the probed structure (sample pattern and accordingly the main pattern) is a deep-trench grating, where the parameter of interest is the trench top-width (equivalently, the parameter of interest can be the line widths).

The test structure 10 includes a main pattern $P_{main}$ formed by a plurality of main features, generally at 22, typically formed by lines L and spaces S, extending along a first longitudinal axis $A_1$ and being spaced from one another along a second lateral axis $A_2$ (pattern axis). As indicated above, the arrangement of main features 22 in the main pattern could be similar to that of the sample pattern, which is to be controlled using the test structure 10, i.e. by optical measurements on the test structure.

Generally, in the sample pattern, the features include at least two different features (e.g. of different geometries) arranged in an alternating fashion. In these examples, these are lines and spaces. The parameter(s) to be controlled may include the lateral dimension (width) L of the line and/or the width W of the space S. In the present example, the test structure is configured for controlling the width W of the space S.

Thus, the test structure includes the main pattern having a main pattern periodicity P (defined by the pitch/period of arrangement of the features/unit cells). The test structure 10 further includes a plurality of auxiliary features 32 (only two such features being shown in the figure) defining at least one auxiliary pattern 30. The auxiliary features 32 are associated with at least some of the main features 22 and are configured such that a lateral dimension of the auxiliary feature 32 is in a predetermined relation with a lateral dimension of the respective main feature 22. In the present example, the auxiliary features 32 are arranged in a spaced-apart relationship along the lateral axis $A_2$ such that a space between two adjacent auxiliary features includes multiple (two or more) main features 22 of the main pattern. Generally speaking, the auxiliary pattern has a pitch $\Lambda$ much larger than the main pattern pitch P.

In the present example, the auxiliary feature 32 is configured as a groove of a substantially V-shaped cross section between two locally adjacent main features 22, and the lateral dimension W of the groove reduces along its depth d from the top surface of main pattern, such that the value of dimension W is a predetermined function of the depth d. Actually, the configuration may be such that the main pattern is in the form of projections (lines) spaced by groove (spaces), as in this example. In this case, some of the grooves (with large periodicity) of the main pattern are modified to have a V-shaped cross section.

Generally, the addition of the periodical arrangement of the auxiliary features 32 (auxiliary patter(s)) modifies the test structure 10 so that every $n^{th}$ space S is narrower (or wider) by $\Delta$, and as a consequence, due to process-related link between trench width and etch depth, is shallower than the other spaces. This design defines a new periodicity of the test pattern, with pitch $$\Lambda = P \cdot n - \Delta$$

Such test structure responds to illumination, in the dark field scheme, by the first diffraction order at angle $$\theta = \sin^{-1}(\sin(\theta_{in}) + \lambda/\Lambda).$$

The value of n is set so that the collection path collects these angles (for a selected wavelengths range). For example, FIG. 4 presents a situation where n=8.

In particular, the value of $\Delta$ can be selected so as to induce higher sensitivity of the test structure to process variation. For example, $\Delta$ can be set so that the trench depth d strongly depends on its width W, e.g. using a small trench width, for which the trench is not fully etched, creating a sharp bottom. Then, small deviations of the patterning process causes an amplified modification to the large-pitch trenches, increasing the dark field signal sensitivity to the parameter of interest (i.e. width W of spaces S between the main features 22).

Figure 5A:
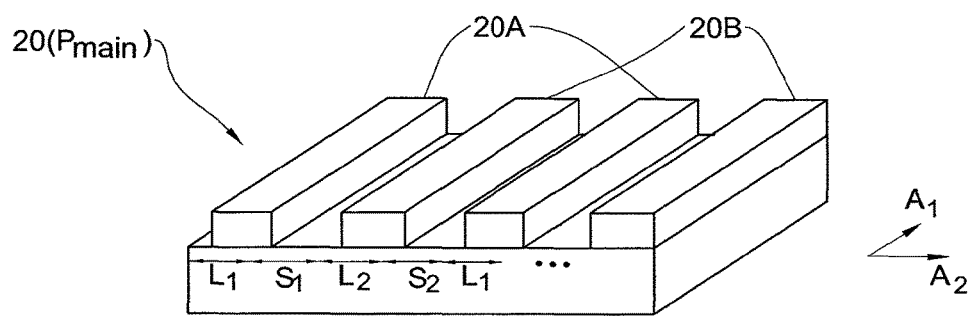
FIGS. 5A to 5C exemplify the principles of configuration of a test structure according to further embodiments of the invention.

A similar approach can be implemented to another application, namely pitch divided gratings. In this connection, reference is made to FIGS. 5A to 5C. FIG. 5A exemplifies a sample pattern 20/main pattern $P_{main}$ in the form of a pitch-divided grating. The main pattern $P_{main}$ is comprised of two interlaced sub-gratings (sub-arrays of main features 22A and 22B) which are nominally identical (equal line widths, L1=L2) and evenly placed (constant spacing between lines, S1=S2).

It should be understood, that generally, the main features of the main pattern may be arranged in more than two arrays in an alternating manner along the lateral axis $A_2$, depending on the manufacturing process.

In this case, the test structure may be designed to create a direct link between high orders diffraction and the parameter(s) of interest. In this approach of designing the test structure, high order(s) diffraction are nominally not collected at all by the collection channel (at least for some wavelength range). Rather, high orders are collected only when the parameter of interest deviates from its nominal value, providing optimal sensitivity and ultra-low background signal.

As a specific example, the pitch division application is considered. In these applications, the fabrication process is designed to provide a periodic structure with half the pitch allowed by a single lithography printing. Examples for such methods are Litho-Etch-Litho-Etch or Spacer Assisted Double Patterning. These techniques are known per se and do not form part of the present invention, and therefore need not be described in details, except to note that pitch-divided structures are characterized by very small pitch, commonly less than 100 nm, and do not support reflection of any high diffraction orders.

These pitch division methods, implemented through multiple patterning, are today and for the foreseeable future, key methods to achieve small-pitch structures, and consequently play an important role in all advanced semiconductor device fabrication. However, these methods introduce a set of challenges to the fabrication process. The pitch division processes are susceptible to errors where the pitch is not divided in a perfect way; one such error is a difference in line widths of the two sub-gratings (L1≠L2), while another is a difference in consecutive trench widths (S1≠S2).

The main challenge involves identification of these differences between the two sub-pitch structures, as standard optical metrology is very weakly sensitive to such discrepancies.

The test structure of the invention, suitable for effectively identifying the above errors, includes the auxiliary features arranged in multiple additional auxiliary patterns, associated with respective multiple arrays of the features of the main pattern. For example, in case of two arrays of the main features, the auxiliary features define two associated auxiliary patterns. The auxiliary features in the auxiliary pattern are arranged in a spaced-apart relationship along the first axis $A_1$, with a pitch significantly larger than that of the main features' array along the second axis $A_2$. Also, the two adjacent auxiliary patterns are shifted with respect to one another other by a predetermined distance along the first axis $A_1$.

Considering for example a situation when the parameter of interest is the discrepancy between the pitch-divided line widths, the metrology is required to provide an accurate measure of L1–L2, where the process is intended to provide nominal difference of 0.

Figure 5B:
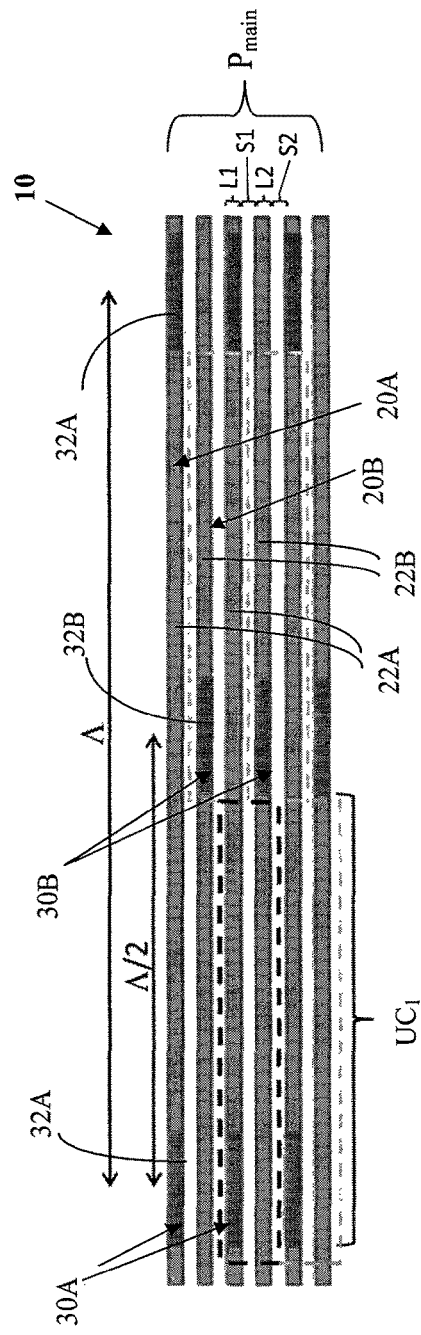
Figure 5C:
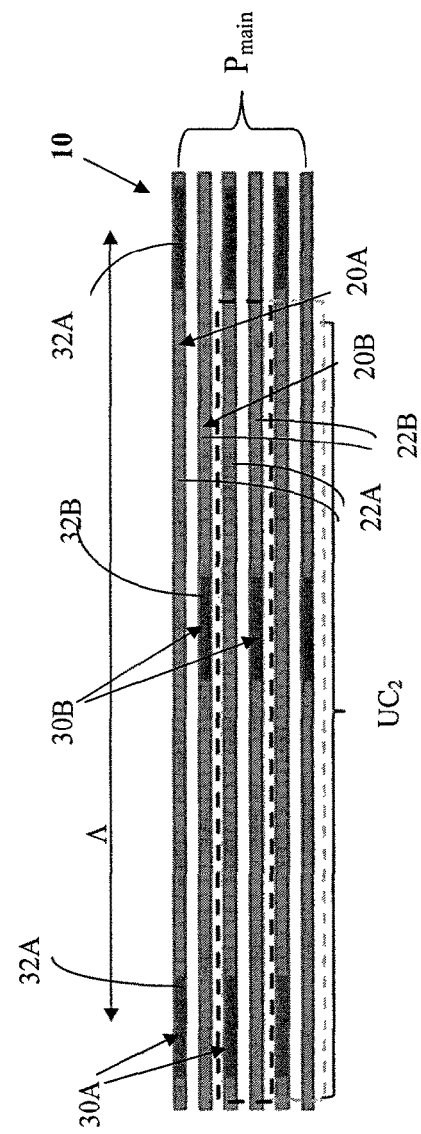

FIGS. 5B and 5C exemplify the test structure (top view), where FIG. 5B shows a nominal design (L1=L2), and FIG. 5C shows the situation when an error in the line width (L1=L2).

In this example, the test structure 10 includes a main pattern $P_{main}$ formed by first and second arrays 20A and 20B of main features 22A and 22B arranged in an interlaced fashion. Lines $L_1$ and $L_2$ of these arrays extend along the first axis $A_1$ and are spaced from one another along the second axis $A_2$. The test structure 10 is modified by adding corresponding first and second auxiliary patterns 30A and 30B, formed by auxiliary features 32A and 32B. The auxiliary features of the pattern are arranged in a spaced-apart relationship with pitch Λ along the main feature (line) of the respective array of the main pattern. The auxiliary features may be configured as vias in the printed lines. This addition of vias (auxiliary features) can be easily implemented, since in any case the wafer (sample) goes through the required fabrication steps following the creation of the lines. It should be understood that creation of such superimposed large-pitch auxiliary pattern(s) is possible using any added auxiliary features to the main pattern, and the test structure configuration is not limited to vias.

Vias 32A, 32B are placed along the lines $L_1$, $L_2$ correspondingly with period Λ. The auxiliary patterns 30A and 30B are shifted with respect to one another along the axis $A_1$ (along the line of the main pattern) a certain distance, e.g. Λ/2.

The vias are placed with periodicity Λ along each line. This periodicity is significantly larger than the original grating pitch (i.e. that of the main pattern), and can be implemented without significant fabrication complexity. The vias in the two auxiliary arrays are displaced by Λ/2 along the axis $A_1$ with respect to each other.

As shown in FIG. 5B, nominally, when L1=L2, a unit cell $UC_1$ (marked by dashed lines) is formed having a width Λ/2, i.e. the periodicity of the entire test pattern along the axis $A_1$ is Λ/2. As shown in FIG. 5C, when the structure deviates from the target design (L1≠L2), the arrangement of the auxiliary features of the two patterns defines a modified unit cell $UC_2$, i.e. the Λ/2 periodicity no longer holds. Instead, the period in the axis $A_1$ is Λ.

It should be noted that the specific design of the auxiliary features, e.g. vias (e.g. their width) can be chosen so as to provide optimal non-zero order(s) (dark field) signal. The lateral dimension of the auxiliary feature (the width of the via at its top) may be substantially equal to that of the respective main feature (line).

Figure 6:
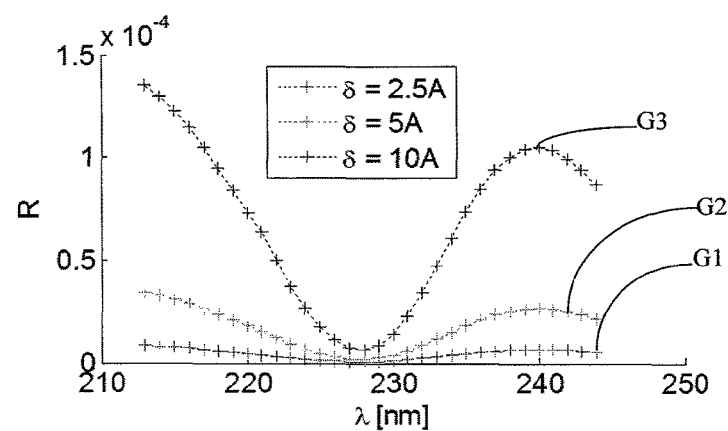
FIG. 6 exemplifies the measured dark field signal for the test structure of FIGS. 5B-5C for different values of process error in the pattern parameter.

Reference is made to FIG. 6 illustrating an example for the calculated dark field spectrum from such test structure 10. In the figure, three graphs G1, G2 and G3 are shown, corresponding, respectively, to three values of L1−L2=δ, being 2.5; 5; 10. For δ=0, the dark field signal is zero, by virtue of this target design and the used dark field scheme. The non-zero order(s) diffraction signal is restricted to a specific wavelength range, as dictated by Eq. 1 above. Although signal intensity is small, the dark-field measurement scheme allows its accurate measurement, due to its ultra-low background (i.e. irrelevant) signal.

The high order(s) dark-field signal I is found to be quadratically proportional to the deviation from the target design, namely $$I \propto (L_1-L_2)^2 = \delta^2. \quad (2)$$

It should be noted that the expected signal provides direct information on deviation from the desired situation of L1=L2. Standard OCD metrology can be applied, in addition to the dark-field scheme, providing information on other properties of interest of the structure.

Figure 7:
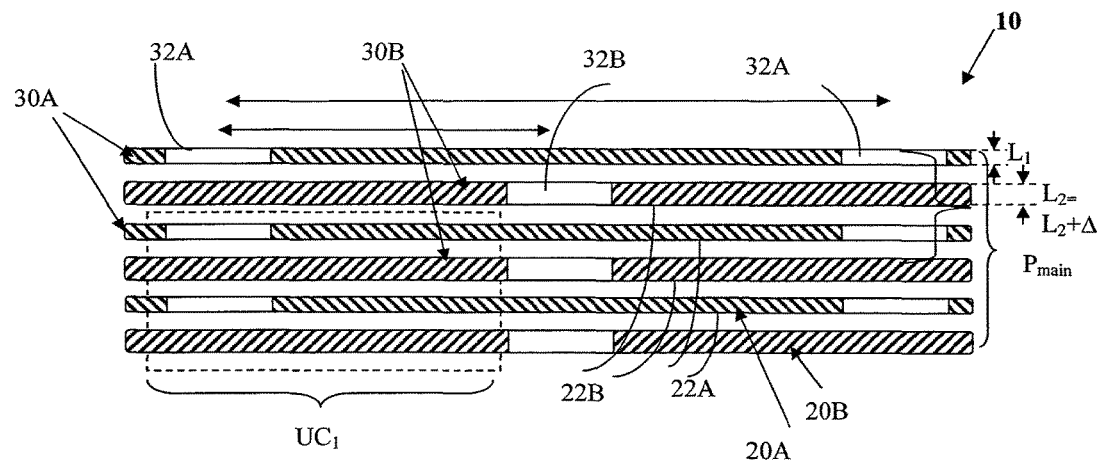
FIG. 7 schematically illustrates a test structure according to yet another example of the invention.

However, the above described measurement does not provide information on the direction of this deviation, i.e. the dark field signal is identical for the situations that L1=L2+δ and L1=L2−δ. This information might be needed to be directly used for the process control. In this case, the test structure can be further modified by intentionally introducing a known difference between the main pattern features of the different arrays. This is exemplified in FIG. 7 showing the test structure 10 configured generally similar to the structure of FIG. 5A, namely including a main pattern $P_{main}$ formed by first and second interlaced sub-patterns 20A and 20B of main features 22A and 22B arranged in an interlaced fashion extending along the first axis $A_1$ and spaced from one another along the second axis $A_2$; and corresponding first and second auxiliary patterns 30A and 30B arranged in a spaced-apart relationship with pitch $\Lambda$ along the main feature (line) of the respective array of the main pattern. However, in this example, instead of using the main features printed at their nominal design, namely L1=L2, an intentional deviation from this nominal situation is used (L1=L2±Δ, with Δ either positive or negative). In this situation, if the process induces a deviation between the two arrays 20A and 20B (sub-gratings) of the main pattern $P_{main}$ so that at the sample pattern L1=L2+δ, in the test structure 10 the deviation will be given by L1=L2+Δ+δ+(δ can be positive or negative).

As explained above, the expected signal is quadratically proportional to L1-L2. In this scheme, the signal is hence given by $$I \propto (L_1 - L_2)^2 = (\Delta + \delta)^2. \quad (3)$$

The intentional deviation Δ is chosen so as to be significantly larger than the expected range of process deviations δ, but still small enough so that the test structure and the sample pattern are similar, and any process errors will cause a similar effect on both of them.

In this situation, the signal is significantly amplified (following the use of large values). Furthermore, there is no longer a discrepancy as to the sign of δ. In this design, however, the main pattern in the test structure intentionally deviates from the sample pattern.

Figure 8:
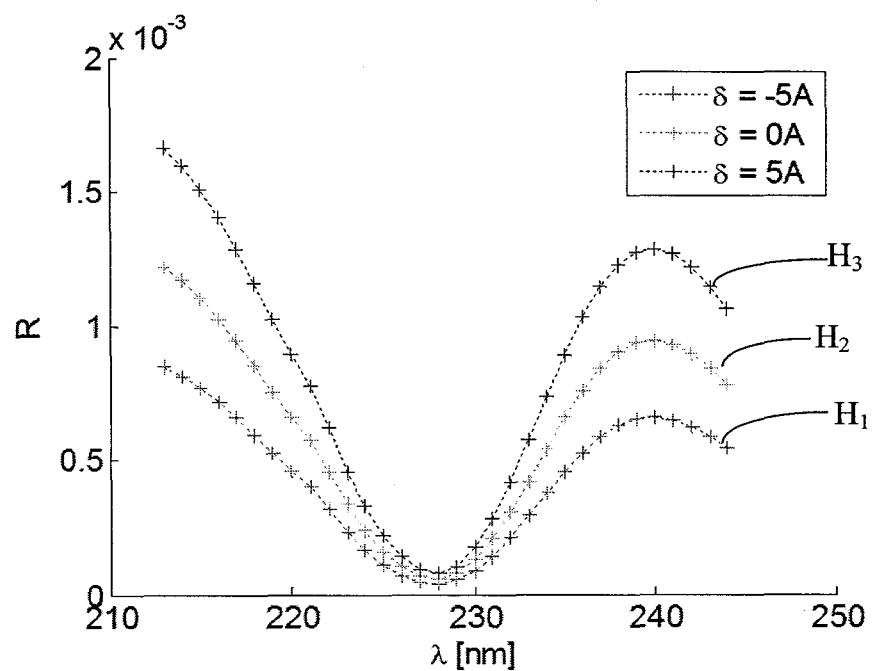
FIG. 8 illustrates the measured dark field signal obtained with the test structure configuration of FIG. 7, for different values of process error in the pattern parameter.

FIG. 8 exemplifies the calculated results for expected dark field spectral signal from such a test structure exemplified in FIG. 7, i.e. the test structure with the intentionally induced deviation (L1=L2+Δ). Three graphs are shown $H_1$, $H_2$ and $H_3$ corresponding to different values of L1−L2=δ being −5, 0, 5. The dark field signal is indeed an order of magnitude larger than in the example with the test structure of FIGS. 5B-5C. In addition, equal process deviations in opposite direction give clearly different signal (have opposite effect on signal intensity), and can be clearly distinguished.

It should be understood that more than one test site with the test structure can be used. This will further reduce sensitivity to measurement errors and noise. For example, the above described test structure with the intentionally induced deviation (L1=L2+Δ) can be used for two test sites, using an intentional offset Δ for one site, and −Δ for the second. Such design has several potential benefits. For example, based on Eq. 3 it is clear that the subtraction between the dark field measurements on these two test structures is proportional to 2Δ·δ. This signal is nominally 0, and linearly proportional to the parameter of interest δ.

According to another example using several test structures, the measurement scheme may utilize collection of the light response of the test structure with different wavelength ranges for different test structures. This facilitates in stabilizing the solution, and prevents error sources, which might arise when using a small wavelength range for the metrology.

The interpretation of the measured dark field signal can be done based on standard OCD methodology. In these methods, the measured signal is compared to nominal/reference signal, which is based on a calculated model (either calculated in real time or based on a pre-calculated library). Different calculated signals are used corresponding to structures with different geometries. A good agreement between the calculated and measured signals indicates that the structure used in the calculated model has dimensions which are in good correspondence with the measured structure.

It is important to note that the above-described technique of the invention based on the specifically designed test structure does not necessarily require such model-based interpretation. Specifically, the dark field measured signal obtained using the test structure of FIGS. 5B-5C, as well as the test structure of FIG. 7 with the intentionally induced deviation (L1=L2+Δ) has a simple dependence on the parameter of interest (Eq. 2, 3). The interpretation of this signal can be done using much simpler methods, namely through a simple proportionality relation. The signal can furthermore be integrated over wavelengths, to provide a single value of total dark field reflectivity. This value directly depends on the parameter of interest. Such integration can reduce noise and error sources considerably.

As described above, the dark field metrology is based on a measurement system by which light is incident on the sample through an optical system, and only non-specular reflections are collected. This approach can be implemented in many ways, and by itself is broadly used in microscopy systems. In practice, it is often beneficial to add a polarizer and\or compensator to the illumination and/or collection channel.

As described above with reference to FIGS. 3A-3B, one possibility for the measurement setup is based on masking the light path. A masking element may be placed before the objective (FIG. 3A), limiting the illuminated regions on the objective and consequently the range of angles that are incident upon the sample. Similarly, such mask partially blocks the return path, limiting the acceptable reflected rays after reflection. This method is based on ascertaining that for every transparent point on the mask, the conjugate point (corresponding to the location to which the ray is reflected) is opaque. Half the objective aperture O is rendered opaque, so that an incoming light ray I which is specularly reflected from a flat surface S is reflected into a point R in the opaque half of the aperture, and is blocked. Only rays having their propagation direction altered by the sample are collected, implementing a dark field (non-zero order(s)) measurement. Alternatively, separate masking of the allowed light paths in the incident and reflected optical paths are used (FIG. 3B).

These approaches, based on a single/common optical path for both illumination and collection, might result that the collected high diffraction modes have a relatively small angle with respect to the incidence direction. This means that the sample pitch is to be extremely large, leading to reduced dark field signal.

As described above with reference to FIGS. 3C-3E, an alternative dark field measurement scheme is based on the use of separate illumination and collection channels. In this approach, a dark field measurement is implemented by illuminating the sample in one direction, and placing the collection/detection channel in an orientation that does not collect light which is specularly reflected from the sample. In FIG. 3C, illumination is incident on the sample in the normal direction and a separate detector is placed at an oblique angle, or vice versa. More generally, the illumination and collection can both have oblique angles with respect to the sample (FIG. 3D) or even be implemented in the same (oblique) optical path (FIG. 3E). The test structure design and the measurement scheme are selected such that the high diffraction orders in the light response of the test structure are directed into the collection path.

Thus, the present invention provides for designing the test structure for use in measurement of the sample pattern, which provides for using a simple dark field measurement scheme to identify a parameter error with high accuracy.

The invention claimed is:

1. A test structure for use in metrology measurements of a sample pattern, the test structure comprising:
   a main pattern formed by a plurality of main features extending along a first longitudinal axis and being spaced from one another along a second lateral axis; and
   a plurality of auxiliary features defining at least one auxiliary pattern, the auxiliary features being associated with at least some of the main features such that a dimension of the auxiliary feature is in a predetermined relation with a dimension of the respective main feature, thereby providing that a change in said dimension of the auxiliary feature from a nominal value affects a change in non-zero order diffraction response from the test structure in a predetermined optical measurement scheme, said change being thus indicative of a deviation in one or more parameters of the main pattern from nominal value thereof, the auxiliary features of the auxiliary pattern being arranged in a spaced-apart relationship along said second lateral axis, a periodicity of the auxiliary pattern being significantly larger than periodicity of the main pattern, the auxiliary feature of the auxiliary pattern comprising a groove of a substantially V-shaped cross section between two locally adjacent features of the main pattern, a lateral dimension of the groove reducing along a depth of the groove from a top surface of said main pattern according to a predetermined function.

2. The test structure according to claim 1, wherein the main features of the main pattern comprise grooves spaced by projections, said auxiliary features being associated with the some of the grooves, modifying them to form said V-shaped cross section.

3. The test structure according to claim 1, wherein said non-zero order of diffraction includes at least one of first and second orders of diffraction.

4. The test structure according to claim 1, wherein said main features are lines arranged with spaces between them.

5. The test structure according to claim 1, configured for controlling a patterning process applied to the sample by monitoring the change of said dimension of the main pattern from the nominal value, said change being indicative of a corresponding deviation of one or more parameters of the sample pattern from the nominal value.

6. A sample comprising a sample pattern and at least one test site, the test site comprising the test structure according to claim 1.

7. The sample according to claim 6, being a semiconductor wafer.

8. The sample according to claim 7, wherein said at least one test site is located in a scribe line of the sample pattern.

9. A method for use in measurements of a sample pattern, the method comprising:
   providing a test structure according to claim 1;
   performing an optical measurement on said test structure and detecting at least one non-zero order diffractive response from the test structure, and generating measured data indicative of said at least one non-zero order diffractive response; and
   processing and analyzing said measured data, and upon identifying a change in the diffractive response, generating data indicative of deviation of one or more parameters of the sample pattern from nominal value.

10. The method according to claim 9, for controlling a patterning process applied to the sample to create said sample pattern.

11. The method according to claim 10, wherein said patterning process comprises at least two sequential patterning stages sequentially creating at least two array of feature forming together said sample pattern.

12. A test structure for use in metrology measurements of a sample pattern, the test structure comprising:
   a main pattern formed by a plurality of main features extending along a first longitudinal axis and being spaced from one another along a second lateral axis; and
   a plurality of auxiliary features defining at least one auxiliary pattern, the auxiliary features being associated with at least some of the main features such that a dimension of the auxiliary feature is in a predetermined relation with a dimension of the respective main feature, thereby providing that a change in said dimension of the auxiliary feature from a nominal value affects a change in non-zero order diffraction response from the test structure in a predetermined optical measurement scheme, said change being thus indicative of a deviation in one or more parameters of the main pattern from nominal value thereof, wherein the auxiliary features of the auxiliary pattern have one of the following configurations: the auxiliary features of the auxiliary pattern are arranged in said spaced-apart relationship along the first longitudinal axis; the auxiliary features of the auxiliary pattern are located in the features of the main pattern and are configured such that the lateral dimension of the auxiliary feature matches the lateral dimension of the respective feature of the main pattern.

13. A sample comprising a sample pattern and at least one test site, the test site comprising the test structure according to claim 12.

14. The test structure for use in metrology measurements of a sample pattern, the test structure comprising:
   a main pattern formed by a plurality of main features extending along a first longitudinal axis and being spaced from one another along a second lateral axis; and
   a plurality of auxiliary features defining at least one auxiliary pattern, the auxiliary features being associated with at least some of the main features such that a dimension of the auxiliary feature is in a predetermined relation with a dimension of the respective main feature, thereby providing that a change in said dimension of the auxiliary feature from a nominal value affects a change in non-zero order diffraction response from the test structure in a predetermined optical measurement scheme, said change being thus indicative of a deviation in one or more parameters of the main pattern from nominal value thereof, wherein said plurality of the auxiliary features defines at least one additional auxiliary pattern, thereby forming at least first and second auxiliary patterns associated with, respectively, said first and second sub-patterns, the auxiliary features of each of said at least first and second auxiliary patterns being arranged in a spaced-apart relationship along the first axis with periodicity significantly larger than a periodicity of the main features of the same sub-pattern along the second axis, and the first and second auxiliary patterns being shifted with respect to each other by a predetermined distance along said first axis.

15. The test structure according to claim 14, wherein the auxiliary patterns have the same periodicity.

16. The test structure according to claim 15, wherein said shift by the predetermined distance is selected to be approximately equal to half of the periodicity of the auxiliary pattern.

17. The test structure according to claim 14, wherein a change in the lateral dimension of the auxiliary feature of one of said at least first and second auxiliary patterns with respect to that of the other auxiliary pattern affects the non-zero order diffraction response from the test structure, being thus indicative of a change in the lateral dimension of the main feature from the nominal value.

18. The test structure according to claim 14, wherein said at least first and second shifted auxiliary patterns define a combined pattern having a unit cell, a change in the lateral dimension of the auxiliary feature of the one of the at least first and second auxiliary patterns with respect to that of the other auxiliary pattern modifying the unit cell of the combined pattern, thereby affecting the non-zero order diffraction response from the test structure, being indicative of a change in the lateral dimension of the main feature from the nominal value.

19. The test structure according to claim 14, wherein the lateral dimensions of the main features of said at least first and second sub-patterns are different from one another by a predetermined value.

20. A sample comprising a sample pattern and at least one test site, the test site comprising the test structure according to claim 14.

21. A test structure for use in metrology measurements of a sample pattern having an arrangement of sample pattern features extending along a first longitudinal axis and being spaced from one another along a second lateral axis, the test structure comprising:
 a main pattern formed by a plurality of main features arranged in accordance with the arrangement of the sample pattern feature; and
 a plurality of auxiliary features associated with at least some of the main features, the auxiliary features being arranged in a spaced-apart relationship along said second lateral axis defining an auxiliary pattern extending along said second lateral axis with a pitch significantly larger than a pitch of the main pattern, the auxiliary feature being configured as a groove of a substantially V-shaped cross section between two locally adjacent features of the main pattern, a lateral dimension of the groove reducing along a depth of the groove from a top surface of said main pattern according to a predetermined function, thereby providing that a change in the lateral dimension of the auxiliary feature from the nominal value affects a change in non-zero order diffraction response from the test structure in a predetermined optical measurement scheme, said change being thus indicative of a deviation in one or more parameters of the main pattern from nominal value thereof.

22. The test structure according to claim 21, wherein the arrangement of the auxiliary features provides that the change in the lateral dimension of the auxiliary feature is indicative of the deviation in the space between the features of the main pattern from a nominal value thereof.

23. A test structure for use in metrology measurements of a sample pattern, the test structure comprising:
 a main pattern corresponding to the sample pattern, the main pattern comprising a plurality of main features extending along a first longitudinal axis and being spaced from one another along a second lateral axis, the main pattern comprising at least first and second sub-patterns defining at least first and second arrays of the main features arranged in an alternating manner along said second lateral axis; and
 a plurality of auxiliary features defining at least first and second periodical auxiliary patterns associated with, respectively, said first and second sub-patterns of the main pattern, the auxiliary features of each of said at least first and second auxiliary patterns being arranged in a spaced-apart relationship along the first axis with periodicity significantly larger than a periodicity of the sub-pattern of the main features along the second axis, and said at least first and second auxiliary patterns being shifted with respect to one another by a predetermined distance along said first axis, the auxiliary features of the auxiliary pattern being located in the features of the main pattern, such that the lateral dimension of the auxiliary feature matches the lateral dimension of the respective main feature, thereby providing that a change in the lateral dimension of the auxiliary feature from a nominal value affects a change in non-zero order diffraction response from the test structure in a predetermined optical measurement scheme, said change being thus indicative of a deviation of one or more parameters of the main pattern from nominal value thereof.

24. A test structure for use in metrology measurements of a sample pattern, the test structure comprising:
 a main pattern corresponding to the sample pattern, the main pattern comprising a plurality of main features extending along a first longitudinal axis and being spaced from one another along a second lateral axis, the main pattern comprising at least first and second sub-patterns defining at least first and second arrays of the main features arranged in an alternating manner along said second lateral axis, wherein the main features of the first and second sub-patterns have lateral dimensions different by a predetermined value; and
 a plurality of auxiliary features defining at least first and second periodical auxiliary patterns associated with, respectively, said first and second sub-patterns of the main pattern, the auxiliary features of the auxiliary pattern being located in the features of the main pattern, such that the lateral dimension of the auxiliary feature matches the lateral dimension of the respective main feature, the auxiliary features of each of said at least first and second auxiliary patterns being arranged in a spaced-apart relationship along the first axis with periodicity significantly larger than a periodicity of the sub-pattern of the main features along the second axis, and said at least first and second auxiliary patterns being shifted with respect to one another by a predetermined distance along said first axis.

* * * * *